United States Patent [19]

Bakas et al.

[11] Patent Number: 4,735,929

[45] Date of Patent: Apr. 5, 1988

[54] CATALYTIC COMPOSITION FOR THE ISOMERIZATION OF PARAFFINIC HYDROCARBONS

[75] Inventors: Steve T. Bakas, Chicago Ridge; Steven W. Cole, Brookfield, both of Ill.

[73] Assignee: UOP Inc., Des Plaines, Ill.

[21] Appl. No.: 932,113

[22] Filed: Nov. 18, 1986

Related U.S. Application Data

[63] Continuation-in-part of Ser. No. 772,099, Sep. 3, 1985, abandoned.

[51] Int. Cl.$^4$ .............................................. B01J 29/20
[52] U.S. Cl. ......................................... 502/66; 502/78
[58] Field of Search .............................. 502/66, 74, 78

[56] References Cited

U.S. PATENT DOCUMENTS

| | | | |
|---|---|---|---|
| 3,562,345 | 2/1971 | Mitsche | 502/78 |
| 3,598,724 | 10/1971 | Mulaskey | 502/78 |
| 4,121,996 | 10/1978 | Hilfman | 502/66 |

FOREIGN PATENT DOCUMENTS

| | | | |
|---|---|---|---|
| 46615 | 3/1982 | European Pat. Off. | 502/78 |

*Primary Examiner*—Carl F. Dees
*Attorney, Agent, or Firm*—Thomas K. McBride; John F. Spears, Jr.

[57] ABSTRACT

Superior isomerization performance is obtained with a catalytic composition comprising a Group VIII noble metal and a hydrogen form mordenite incorporated with alumina. The superior performance is a direct result of the catalyst composition having a surface area of at least 580 m$^2$/g. A novel method of preparing an isomerization catalyst having a surface area of at least 580 m$^2$/g is characterized by contacting a formed catalytic composite with an acidic aqueous solution prior to addition of the Group VIII noble metal.

14 Claims, 1 Drawing Sheet

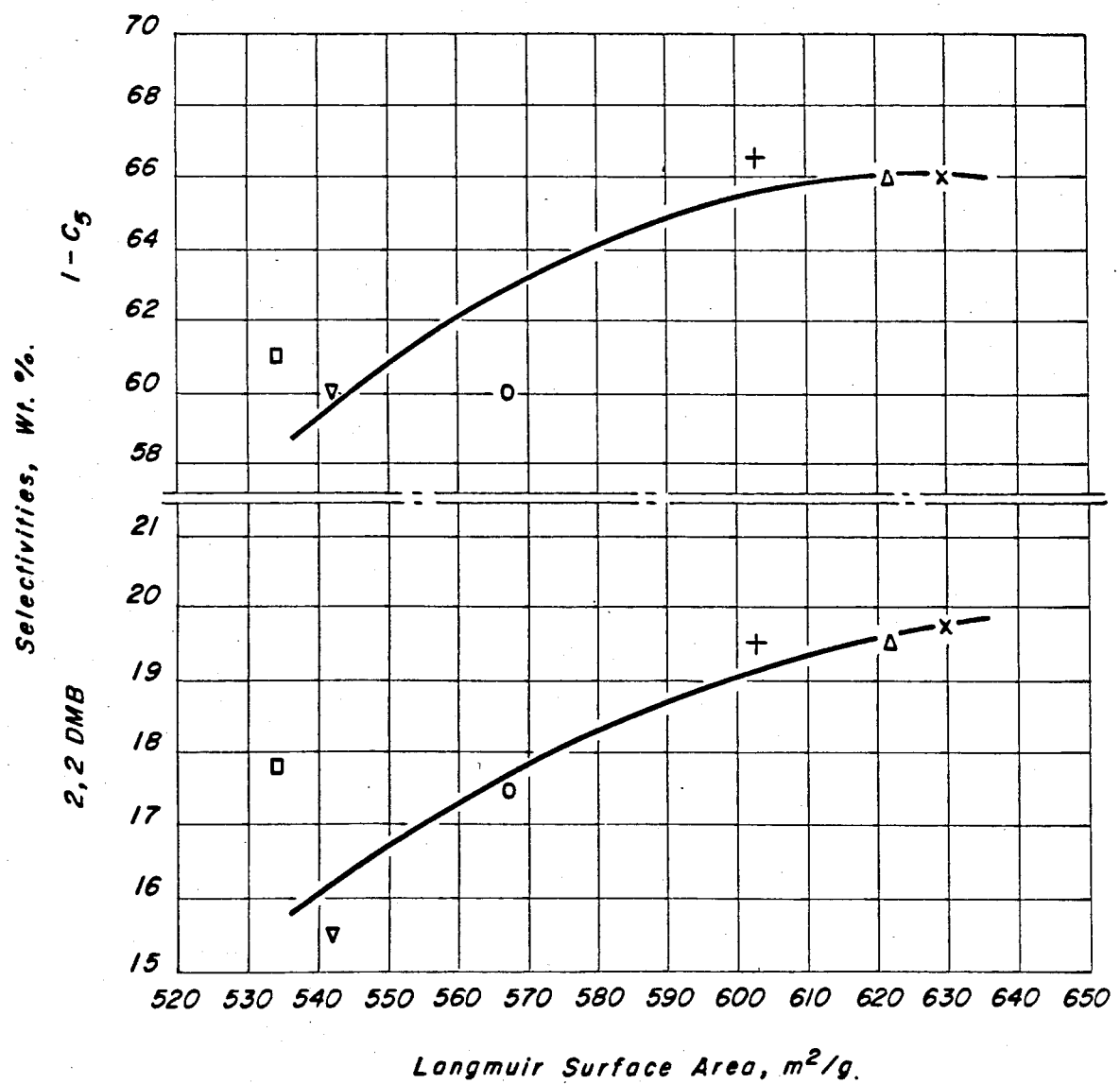

CATALYTIC COMPOSITION FOR THE ISOMERIZATION OF PARAFFINIC HYDROCARBONS

CROSS-REFERENCE TO RELATED APPLICATION

This application is a continuation-in-part of prior copending application Ser. No. 772,099 filed Sept. 3, 1985, now abandoned, the contents of which are incorporated herein by reference thereto.

BACKGROUND OF THE INVENTION

The present invention is related to an improved catalytic composition and a hydroisomerization process employing that catalytic composition. More particularly, this invention involves an isomerization catalyst composition comprising a hydrogenation function selected from the Group VIII metals, a hydrogen form crystalline aluminosilicate zeolite, and a refractory inorganic oxide.

The isomerization of low molecular weight normal paraffins is well established in the art. This reaction is of considerable importance in the petroleum industry because of the substantially higher octane numbers of isoparaffins compared to their normal paraffin counterparts. Since gasoline blends require a distribution of boiling range materials, the isoparaffins in the $C_4$–$C_7$ range are valuable blending components. It has been the practice up until this time to isomerize paraffins to equilibrium mixtures of their branched chain isomers with a variety of catalysts. Friedel-Crafts catalysts, such as aluminum chloride, are known to be effective isomerization catalysts. Noble metals, such as platinum supported on halogenated alumina or silica alumina have also been used effectively to isomerize hydrocarbons. More recently, crystalline aluminosilicate zeolites which have shown catalytic activity have been effectively used in the isomerization of hydrocarbons. Both natural and synthetic crystalline aluminosilicates have been employed. Included among these are the Type X and Type Y zeolites as well as synthetic mordenite.

Specifically, the zeolites known as mordenites have received great attention. Mordenites are crystalline natural or synthetic zeolites of the aluminosilicate type; generally, they have a composition expressed in moles of oxide of

$1.0\pm0.2\ Na_2O.Al_2O_3.10\pm0.5\ SiO_2;$ the quantity of $SiO_2$ may also be larger. Instead of all or part of the sodium, other alkali metals and/or alkaline earth metals may be present.

In general, it has been found that the sodium form of mordenite is not particularly effective for isomerization of hydrocarbons and that replacing all or, for the greater part, the sodium cations with hydrogen ions yields the more advantageous hydrogen form mordenite. Conversion of the sodium form to the hydrogen form can be accomplished by a number of means. One method is the direct replacement of sodium ions with hydrogen ions using an acidified aqueous solution where the process of ion exchange is employed. Another method involves substitution of the sodium ions with ammonium ions followed by decomposition of the ammonium form using a high temperature oxidative treatment.

The activity and selectivity of hydroisomerization catalysts depend on a variety of factors, such as the mode of catalyst preparation, the presence or absence of promotors, quality of raw materials, feedstock quality, process conditions, and the like. Suitable catalysts can be conventionally prepared by combining commercially available crystalline zeolites, such as, a hydrogen form mordenite, with a suitable matrix material followed by the addition of a Group VIII metal, and thereafter activating by conventional means. A new catalyst has been discovered which exhibits greatly improved isomerization performance when compared to conventionally prepared catalysts.

OBJECTS AND EMBODIMENTS

Accordingly, there is provided a catalyst composition for the isomerization of isomerizable hydrocarbons, which comprises a Group VIII noble metal, hydrogen form mordenite, and from about 5 to 25 wt. % alumina, with said catalyst composition having a surface area of at least 580 $m^2/g$. Platinum is the preferred Group VIII metal, and is preferably present in the amount of from 0.15 to 0.5 wt. % of said composition. It is preferred that the mordenite has a silica to alumina ratio of at least 16 and is present in an amount from 75 to 95 wt. % of said composition. The preferred form of the alumina is selected from the group consisting of gamma-alumina, eta-alumina, and mixtures thereof.

In another aspect, the invention is a method of manufacturing the aforementioned catalyst composition. Manufacturing of the catalyst comprises forming a composite comprising hydrogen form mordenite and from about 5 to 25 wt. % alumina, thereafter contacting formed composite with an acidic aqueous solution, followed by incorporation of a Group VIII metal into the formed composite.

These, as well as other embodiments of the present invention, will become evident from the following, more detailed description.

INFORMATION DISCLOSURE

The prior art recognizes a myriad of catalyst formulations for the isomerization of hydrocarbons. It is well known that acids, such as, strong mineral acids, can be used to modify crystalline aluminosilicate zeolite powders through decationization and dealumination. Ammonium compounds have also been successfully employed to convert crystalline aluminosilicates from alkali and/or alkaline metal cation form to the hydrogen form. Combinations of zeolite and refractory inorganic oxide have been disclosed, however, the art is silent as to the inherent problem of loss of the zeolite surface as a result of dilution and forming technique associated with the refractory inorganic oxide.

Combinations of the acid and ammonium treatments have been disclosed for use on aluminosilicate powders. U.S. Pat. No. 3,475,345 (Benesi) discloses a method of converting aluminosilicate zeolites, particularly a sodium form synthetic mordenite, to the hydrogen form utilizing a three-step pretreatment performed on the powdered zeolite. These pretreatment steps consist of (1) a hot acid treatment, (2) a cold acid treatment, and (3) treatment with an ammonium compound. U.S. Pat. No. 3,442,794 (Van Helden et al.) also discloses a method for the pretreatment of aluminosilicate zeolites to the hydrogen form. Again, the preferred zeolite is the synthetic sodium form of mordenite. The method disclosed is very similar to U.S. Pat. No. 3,475,345 mentioned above, with the distinguishing feature being a separately performed two-step pretreatment with (1) an acid compound, and (2) an ammonium compound in arbitrary order. An important feature of both references is that the treatments are performed solely on the aluminosilicate zeolite with the express intention of modifying said zeolite before being utilized in a catalyst formulation and that no mention of the importance of the surface area of the catalytic composite is disclosed. This is distinguished from the present invention in that any treatment performed is subsequent to the zeolite being incorporated into a formed catalyst composite and more importantly without any apparent modification of the zeolite itself.

Treatment of the aluminosilicates with acid have not only been effective for conversion to the hydrogen form, but also have been used as a means for increasing the silica to alumina ratio. Typically, a silica to alumina ratio of about 10:1 is observed for a sodium form synthetic mordenite and is substantially unchanged if an ammonium treatment is used to convert the mordenite to the hydrogen form. If a mordenite powder is subjected to an acid treatment as taught in U.S. Pat. No. 3,597,155 (Flanigen), an increase in the silica to alumina ratio is effected. The acid treatment is believed to cause a reduction of the framework tetrahedra aluminum atoms, thus increasing the proportion of silicon atoms present in the zeolitic structure. Isomerization performance is enhanced when the silica to alumina ratio of a mordenite powder is increased. As taught in U.S. Pat. No. 3,507,931 (Morris et al), a silica to alumina ratio above about 20:1 significantly improves the isomerization of light hydrocarbons. U.S. Pat. No. 4,018,711 (Bertolacini) also teaches that isomerization performance is improved if a pretreated mordenite powder having a silica to alumina ratio of at least 19:1 is incorporated in a catalytic composition. Again, these references specifically teach the use of acid treatment on the zeolite powder alone for the purpose of increasing the silica to alumina ratio, whereas the subject invention incorporates an already high silica to alumina ratio crystalline aluminosilicate into the catalytic composite. These references also do not teach the importance of the surface area of the catalytic composite or its relationship to isomerization performance.

A common attribute of the above mentioned prior art is that, in all cases, the crystalline aluminosilicate alone, in particular the synthetic sodium form of mordenite, is subjected to an acid and/or an ammonium pretreatment step(s) to modify the aluminosilicate before its incorporation into the catalyst composition. Although the pretreatment of mordenite as described in the above references enhances the isomerization performance of catalytic composites comprising such pretreated mordenite, further improvements are still obtainable.

BRIEF DESCRIPTION OF THE DRAWING

Reference to the accompanying drawing will facilitate understanding of the present invention. The graph shown in the drawing illustrates that the isomerization performance is a function of the Langmuir surface area of the catalyst composition. The isomerization performance is characterized as selectivity to desired products, namely, 2,2 dimethylbutane (2,2 DMB) and isopentane (i-$C_5$).

DETAILED DESCRIPTION

While previous work dealt exclusively with pretreatment of the aluminosilicate component of an isomerization catalyst, it is one of the objects of the present invention to provide a novel catalyst composition which is characterized by exceptionally high surface area and which exhibits improved isomerization performance.

According to the present invention, there is provided a catalyst composition for the isomerization of isomerizable hydrocarbons into their branched chain equivalents and a method of manufacturing said catalyst composition.

The catalyst composition of the present invention comprises a Group VIII noble metal, hydrogen form mordenite, and from about 5 to 25 wt. % alumina with said catalyst composition having a surface area of at least 580 $m^2/g$. We have found that significant improvements in isomerization performance are realized when the surface area of the catalyst composition is at or above 580 $m^2/g$. Although a maximum surface area of the catalyst composition has not been determined experimentally, it is believed that an upper limit of 700 $m^2/g$ is possible. Obtaining such a high surface area in the range from about 580 to 700 $m^2/g$ is the object of one of the embodiments of the subject invention and is further illustrated in subsequent examples.

The metal that is present in the catalyst composition to supply the hydrogenation-dehydrogenation function is a Group VIII noble metal. The Group VIII noble metals include the metals of the "Platinum Series" and the metals of the "Palladium Series", i.e., platinum, iridium, osmium, palladium, rhodium, and ruthenium. The preferred Group VIII noble metal is platinum. The Group VIII noble metal of the catalytic composition of the present invention will be utilized in an amount from about 0.1 to about 5% by weight of the composition. It is particularly preferred that the metal component be at least about 0.15% by weight and not over 0.5% by weight.

Of course, it is not beyond the scope of the instant invention that the catalyst composition contain a catalytically effective amount of a promoter metal. Examples of such promoter metals include tin, lead, germanium, cobalt, nickel, iron, tungsten, chromium, molybdenum, bismuth, indium, gallium, cadmium, zinc, uranium, copper, silver, gold, tantalum, one or more of the rare earth metals, and mixtures thereof.

Another essential component of the instant invention is the hydrogen form mordenite. While mordenite is naturally occurring, a variety of synthetic mordenites are available commercially, usually in a powder form. These synthetic mordenites can be obtained in both the sodium form and hydrogen form and at varied silica to alumina ratios. It is a preferred embodiment of the present invention that the mordenite be of the hydrogen form and that the silica to alumina ratio be at least 16:1, more specifically, in the range from 16:1 to 60:1. The pretreatment steps taught in the aforementioned references are routinely and typically employed in the manufacture of commercially available mordenite powders which meet the requirements as a starting material as set forth in the present invention. These pretreatment steps are used to increase the silica to alumina ratio of the mordenite zeolite and to convert the sodium form to the more desirable hydrogen form.

The hydrogen form mordenite is incorporated with alumina and formed into a catalytic composite. The formed catalytic composite may be prepared by any known method in the art including the well-known oil drop and extrusion methods. The hydrogen form mordenite may be present in an amount within the range of 50 to about 99.5 wt. %, preferably within the commercially desirable range of 75 to about 95 wt. %. Thus, the alumina is preferably present in an amount within the range of from about 5 to about 25 wt. %, based on total weight of the catalyst composition.

The preferred alumina for use in the present invention is selected from the group consisting of gamma-alumina, eta-alumina, and mixtures thereof. Most preferred is gamma-alumina. Other refractory inorganic oxides which are contemplated include, for example, silica gel, silica-alumina, magnesia-alumina, zirconia alumina, phosphorus-containing alumina, and the like.

Surprisingly and unexpectedly, it has been found that a catalyst composition prepared in accordance with and containing the components as claimed in the invention will possess a surface area higher than any catalyst heretofore described in the art. This high surface area of at least 580 m$^2$/g is surprising when one considers not only the diluting affect of an alumina support material having relatively low surface area (maximum approximately 250 m$^2$/g), but also considering the lowering of surface area caused by the particular forming technique employed. As exemplified herein below, catalyst of the prior art do not obtain the high surface area of the instant catalyst and thus demonstrate inferior performance, particular as isomerization catalyst. The prior art does not teach or suggest how to obtain a mordenite/alumina catalyst having a surface area of at least 580 m$^2$/g. Surface area, as referred to herein, is determined by employing the Langmuir method of correlating adsorption/desorption isotherm data. The Langmuir method is especially suitable for catalytic composites containing high percentages of crystalline aluminosilicates. The data needed for the Langmuir method is typically obtained by well known adsorption/desorption apparatuses, preferably a nitrogen adsorption/desorption apparatus. Therefore, the present invention allows for a catalyst composition having a high surface area mordenite without loss of this surface area when formed with alumina to give a commercially acceptable formulation. Likewise, the benefit of the presence of alumina, which imparts, among other things, strength to the catalyst composition, may be achieved without penalty with regard to the surface area of the mordenite.

Any method may be employed which results in a final catalyst composite having at least a surface area of 580 m$^2$/g. Catalyst compositions with high surface areas can be arrived at in a number of ways, such as, using a hydrogen form mordenite powder which inherently has a very high surface area, or by having one component of the composite, which has a high surface area, in great proportion to other components. A preferred method of achieving a surface area of at least 580 m$^2$/g is to contact the formed catalytic composite with an acidic aqueous solution. This acidic aqueous solution may contain ammonium ions. The formed catalyst composite may be dried and/or calcined prior to its contact with the aqueous solution.

The acidic nature of the aqueous solution is attained by employing an acid. Particularly suitable are strong mineral acids such as $H_3PO_4$, $H_2SO_4$, $HNO_3$, and HCl. HCl is the preferred acid of the present invention. Of course, it is contemplated that mixtures of various acids may also be employed. If the acidic aqueous solution contains ammonium ions, the preferred source of these ions is $NH_4Cl$, but any ammonium compound which can form ammonium ions, such as $NH_4OH$, $NH_4NO_3$, $NH_4$ sulfates, $NH_4$ phosphates and the like, should be suitable.

Concentrations of the acid and ammonium ions in the aqueous solution are not critical and can vary from 0.5M to 6M for the acid concentration and 0.5M to 4M for the ammonium ion concentration. Particularly good results are obtained using a solution containing acid and ammonium ion concentrations within the range of 2 to 5M for the acid and 1 to 3M for the ammonium ion.

A plurality of methods for contacting the formed catalytic composite and the acidic aqueous solution is envisioned with no one method of particular advantage. Such contacting methods may include, for example, a stationary catalyst bed in a static solution, a stationary catalyst bed in an agitated solution, a stationary catalyst bed in a continuously flowing solution, or any other means which efficiently contacts the catalyst composition with the acidic aqueous solution.

The temperature of the contacting solution should be within the range of 25° C. (77° F.) to about 100° C. (212° F.), preferably within the range of from about 50° C. (122° F.) to about 98° C. (208° F.) The time required for the contacting step will depend upon concentrations, temperature and contacting efficiency. In general, the contacting time should be at least 0.5 hour, but not more than 4 hours, preferably between 1 and 3 hours in duration.

As a result of contacting the formed catalytic composite with the acidic aqueous solution, an increase in the measured surface area is observed. Surprisingly and unexpectedly, this increase in surface area, to 580 m$^2$/g or higher, is not accompanied by an increase in the silica to alumina ratio of the hydrogen form crystalline aluminosilicate as measured by Magic Angle Spinning NMR (MASNMR). The MASNMR technique, which is a well known analytical method of the art, indicates no reduction in the framework tetrahedral aluminum atoms of catalyst compositions of the present invention. Although it is not certain the exact reason why the surface area is higher after contacting the formed catalytic composite, it is believed that the acidic aqueous solution is removing occluded ions from the mordenite which are deposited therein as a result of the forming technique employed.

The catalyst of the invention has particular utility for the isomerization of isomerizable hydrocarbons. Included in the group of isomerizable hydrocarbons are saturated hydrocarbons including paraffin hydrocarbons and is still more particularly suitable for the hydroisomerization of straight chain or slightly branched chain paraffins containing four or more carbon atoms per molecule. The isomerization reaction can be conducted over a wide range of temperatures, but, in general, in the range from about 93° C. (200° F.) to about 427° C. (800° F.). Space velocities from about 0.25 to about 5 liquid volumes per hour of said isomerizable hydrocarbons per volume of said catalytic composite are preferred with reaction zone pressures preferably within the range from about 6.9 bar (100 psi) to about 69 bar (1000 psi). It is particularly desirable to carry out the isomerization reaction in the presence of hydrogen preferably in the range from about 0.5 to about 5 moles of $H_2$ per mole of isomerizable hydrocarbon. The function of the hydrogen is primarily to improve catalyst life, apparently by preventing polymerization of intermediate reaction products which would otherwise polymerize and deposit on the catalytic composite. It is not necessary to employ pure hydrogen since hydrogen containing gases, e.g., hydrogen-rich gas from the catalytic reforming of naphthas are suitable.

The following examples are presented for purposes of illustration only and are not intended to limit the scope of the present invention.

A number of experiments were conducted to study how changes in the surface area of isomerization catalyst composites affect isomerization performance. Six catalysts were prepared for evaluation. In all the catalyst preparations described in the following examples, the starting material was the hydrogen form, low sodium, partially dealuminated synthetic mordenite powder (marketed by Union Carbide under the name LZ-M-8), hereinafter referred to as the as received mordenite.

EXAMPLE I

In this example, the method of formulating the catalyst, designated as Catalyst A, was not in accordance with the subject invention. A 9:1 weight ratio mixture of as received mordenite and alumina was admixed with an acidified peptization solution and extruded by means known in the art. The extruded composite was dried, calcined in an oxidative atmosphere, impregnated with platinum, and calcined again. The platinum was added to a level of 0.324 wt. %, based on the weight of the finished catalyst. A surface area of 567 $m^2/g$ was measured for Catalyst A and correlated against its isomerization performance. This correlation is shown graphically in the attached drawing.

EXAMPLE II

The catalyst composite of this example was designated as Catalyst B and was also not made in accordance with the subject invention. The as received mordenite powder was contacted with an acidic aqueous solution containing ammonium ions comprising 10 wt. % HCl and 10 wt. % $NH_4Cl$ at 140° F. (60° C.) for 150 minutes at a solution to zeolite weight ratio of 5:1. The resulting mordenite powder was washed with $H_2O$ and calcined prior to admixture with alumina and peptization solution. Extrusion and platinum addition were performed in an equivalent manner for Catalyst B as for Catalyst A of Example I. The platinum level of Catalyst B was 0.321 wt. %. A surface area of 534 $m^2/g$ was measured for Catalyst B and correlated against isomerization performance as shown in the attached drawing.

EXAMPLE III

Catalyst C made in accordance with the invention was formulated substantially in the same manner as Catalyst A of Example I. However, in accordance with the subject invention, the dried extrudate prior to calcining and platinum addition was contacted with an acidic aqueous solution containing ammonium ions. This solution contained 10 wt. % HCl and 10 wt. % $NH_4Cl$. Contacting of the solution and the extrudate was performed at 140° F. (60° C.) for 120 minutes at a solution to zeolite weight ratio of 25:1. The extrudate was subsequently dried, calcined and treated with platinum following the same procedures used for Catalysts A and B. Catalyst C had a platinum level of 0.396 wt. %. A surface area of 622 $m^2/g$ was measured for Catalyst C and correlated against its isomerization performance as shown in the attached drawing.

EXAMPLE IV

The calcined catalyst composite of Example II prior to platinum addition, was subjected to a second contact with an acidic aqueous solution in the manner as was Catalyst C in Example III. This second contact of the formed composite with the acidic aqueous solution is in accordance with the subject invention. Platinum was then added to the composite to a level of 0.308 wt. % and designated as Catalyst D. A surface area of 630 $m^2/g$ was measured for Catalyst D and correlated against its isomerization. This correlation is illustrated in the accompanying drawing.

EXAMPLE V

Catalyst E was formulated in the same manner as Catalyst A except that the acidity of the peptization solution was reduced by 90%. As in Example I, Catalyst E was not formulated in accordance with the present invention. Catalyst E had a platinum level of 0.313 wt. %. A surface area of 542 $m^2/g$ for Catalyst E was measured and correlated against its isomerization performance test results. This correlation is shown in the attached drawing.

EXAMPLE VI

Catalyst F made in accordance with the invention was formulated in the same manner as Catalyst C of Example III. However, during preparation of Catalyst F, the dried extrudate was contacted with an acidic aqueous solution not containing ammonium ions. This solution contained 3.0 wt. % HCl. Contacting of the solution and the extrudate was performed at 140° F. (60° C.) for 120 minutes at a solution to zeolite weight ratio of 12:1. The extrudate was subsequently dried, calcined, and treated with platinum. Catalyst F had a platinum level of 0.298 wt. %. A surface area of 603 $m^2/g$ was measured for Catalyst F and correlated against its isomerization performance as shown in the attached drawing.

EXAMPLE VII

The six catalyst formulations of Examples I through VI consisting of platinum supported on a hydrogen form mordenite gamma-alumina composite were evaluated for isomerization performance in a flow reactor processing a feed comprising a mixture of 46 wt. % n-pentane, 47.0 wt. % n-hexane, 5.5 wt. % methyl cyclopentane, and 1.5 wt. % benzene.

The operating conditions used to test the isomerization performance of Catalysts A through F comprised a reactor pressure of 21.7 bar (315 psia), a liquid hourly space velocity of 1.0 $hr^{-1}$, a $H_2$ to feed hydrocarbon molar ratio of 1.0 and temperatures ranging between 254° C. (490° F.) and 277° C. (530° F.) Test run data, specifically the selectivities to iso-pentane (i-$C_5$) and to 2,2-dimethyl butane (2,2 DMB) at 97 wt. % $C_5^+$ yield, were used as measures of isomerization performance. The selectivity value for i-$C_5$ presented in the accompanying drawing is defined as the weight fraction of the i-$C_5$ in the liquid isomerization product divided by the weight fraction of the total amount of $C_5$ hydrocarbon in the product. To obtain the 2,2 DMB selectivity value shown in the drawing, the weight fraction of 2,2 DMB in the liquid isomerization product is divided by the total, non-cyclic, $C_6$ hydrocarbon in the product.

At the isomerization test run conditions utilized in the above examples, the selectivities to i-$C_5$ and 2,2 DMB are a direct function of the measured surface area of the finished catalyst. As graphically illustrated in the attached drawing, the selectivities to i-$C_5$ and 2,2 DMB increase as the measured surface area increases. Catalyst C of Example III, Catalyst D of Example IV, and Catalyst F of Example VI all demonstrate the highest selectivities to i-$C_5$ and 2,2 DMB in accordance with the invention, all having measured surface areas of at least 580 $m^2/g$. Comparison of the platinum levels of Catalysts C and D to each other and to the other three catalysts shows that the platinum level does not correlate with isomerization performance further substantiating the benefit of having catalyst composites with surface areas of at least 580 $m^2/g$. Thus, utilizing the catalytic composition of the present invention clearly yields catalysts with superior isomerization performance.

What is claimed is:

1. A catalytic composite comprising in combination a Group VIII noble metal component and a support comprising hydrogen form mordenite dispersed in an alumina matrix, said composite comprising from about 5 to 25 percent by weight of alumina and wherein said support is contacted with an acidic aqueous solution after it is formed and prior to addition of the Group VIII noble metal component, said contacting occurring at conditions selected to increase the surface area of the composite to at least 580 $m^2/g$ without increasing the silica/alumina ratio of the mordenite.

2. The catalytic composite of claim 1 wherein said composite is spherical, cylindrical and/or granular in shape.

3. The catalytic composite of claim 1 wherein said alumina is selected from the group consisting of gamma-alumina, eta-alumina, and mixtures thereof.

4. The catalytic composite of claim 1 wherein said alumina is gamma-alumina.

5. The catalytic composite of claim 1 wherein the hydrogen form mordenite has a silica to alumina ratio of at least 16:1.

6. The catalytic composite of claim 1 wherein the Group VIII noble metal is platinum and is present in an amount of from 0.15 to 0.5 percent by weight based on the catalytic composite.

7. The catalytic composite of claim 1 wherein the support is formed by extrusion.

8. A method of manufacturing a catalytic composite comprising in combination a Group VIII noble metal component and a support comprising hydrogen form mordenite dispersed in an alumina matrix, said composite comprising from about 5 to 25 percent by weight of alumina, said method comprising forming said support, contacting said formed support with an acidic aqueous solution prior to addition of said Group VIII noble metal component under conditions selected to increase the surface area of the composite to at least 580 $m^2/g$ without increasing the silica/alumina ratio of the mordenite and subsequently adding said Group VIII noble metal component.

9. The catalytic composite of claim 8 wherein said composite is spherical, cylindrical and/or granular in shape.

10. The catalytic composite of claim 8 wherein said alumina is selected from the group consisting of gamma-alumina, eta-alumina, and mixtures thereof.

11. The catalytic composite of claim 8 wherein said alumina is gamma-alumina.

12. The catalytic composite of claim 8 wherein the hydrogen form mordenite has a silica to alumina ratio of at least 16:1.

13. The catalytic composite of claim 8 wherein the Group VIII noble metal is platinum and is present in an amount of from 0.15 to 0.5 percent by weight based on the catalytic composite.

14. The catalytic composite of claim 8 wherein the support is formed by extrusion.

* * * * *